Nov. 16, 1965 E. W. SAGE Plant Pat. 2,571
PLUM TREE
Filed May 27, 1964
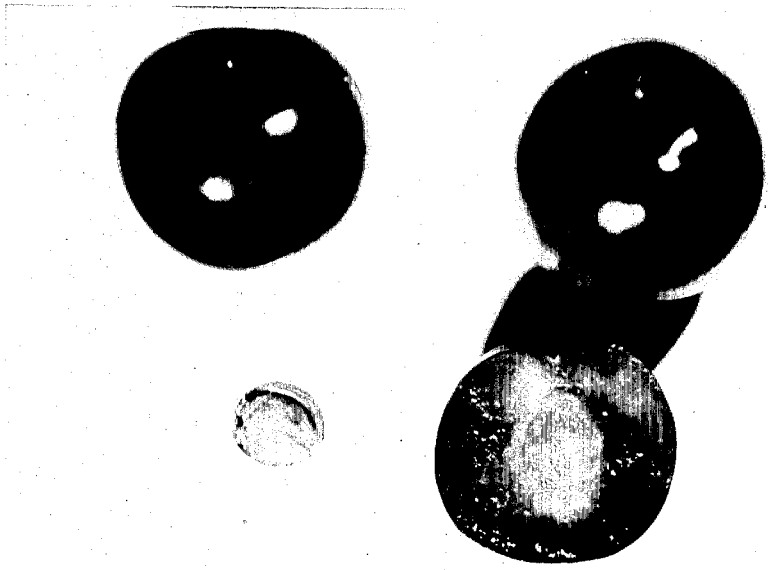
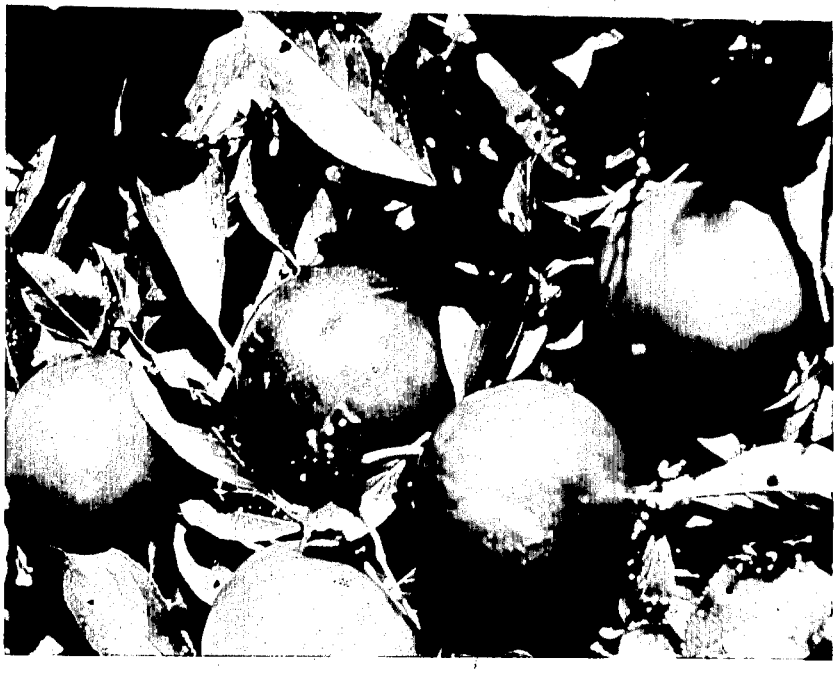
Inventor.
Ernest W. Sage
By: Robb & Robb
Attorneys.

United States Patent Office

Plant Pat. 2,571

Patented Nov. 16, 1965

2,571

PLUM TREE

Ernest W. Sage, Ohaupo, Hamilton, New Zealand, assignor to Stark Bro's Nurseries & Orchards Company, Louisiana, Mo., a corporation of Missouri Filed May 27, 1964, Ser. No. 370,745
1 Claim. (Cl. Plt.—38)

The present invention relates to a new and distinct variety of plum tree which was discovered by me as a selected seedling of unknown parentage, on my cultivated orchard property located at Ohaupo, Hamilton, New Zealand.

At the time of my discovery aforesaid, my selection of this new seedling was prompted by the general resemblance of both the tree and fruit to the tree and fruit of the variety known in New Zealand as "Purple King" or "Maynard" (both unpatented), while the fruit of the new variety was characterized by a red flesh color throughout, instead of the yellow flesh color with a layer of red color immediately beneath the skin as characteristic of "Purple King" or "Maynard." Further observations and tests of the new variety established that the fruit was also superior in flavor to that of "Purple King" or "Maynard," as well as having very good resistance to *Xanthomonas pruni* spot, which is a bacterial disease which is very difficult to control by spraying or by other cultural practices. I have also established that my new variety has good resistance to other diseases to which plum varieties in general are normally subject in New Zealand.

A sexual reproduction of my new variety, as performed by me by budding at Ohaupo, New Zealand, shows that the foregoing characteristics and distinctions come true and are established and transmitted through succeeding propagations. Despite the uncertainty of the parentage of my new seedling, I am convinced that it represents a new and distinct variety, and is differentiated from all other varieties by the unique combination of characteristics referred to in the foregoing.

The accompanying drawing shows typical specimens of the fruit, stone and foliage of my new variety of plum tree as depicted in color as nearly true as it is reasonably possible to make the same in a color illustration of this character, with one of the fruit specimens being shown in cross-section, and with a typical specimen stone being depicted separately in elevation.

The following is a detailed description of my new variety, with terminology in accordance with the Horticultural Color Chart published in collaboration with The Royal Horticultural Society, except where general color terms of ordinary dictionary significance are obvious:

Locality where grown and observed: Ohaupo, Hamilton, New Zealand.

Dates of first and last pickings: January 19 and January 28, respectively.

Tree: Large size; vigorous; dense; upright; round-topped; hardy; very productive; uncertain bearer.

*Trunk.*—Stocky; shaggy.

*Branches.*—Stocky; medium smoothness.

*Color.*—Dull brown.

*Lenticels.*—Few; small.

*Leaves.*—Medium size; oval; pointed; medium thickness; smooth. Length—about 4 inches. Width—about 1¾ inches. Color—medium green. Margin—finely serrate. Petiole—long; medium thickness. Glands—usually average 2 in number; opposite; small; globose; free.

Flowers: Mid-season in time as compared with other varieties grown in the same locality; medium size.

*Dates of first and full bloom.*—August 24 and September 11, respectively, with blooming period ending about September 28 at Ohaupo, New Zealand.

*Color.*—White.

Fruit:

*Maturity when described.*—Eating ripe (January 24).

*Size.*—Large. Axial diameter—about 2 inches. Transverse diameter—about 2½ inches. Diameter at right angles to suture plane—about 2½ inches.

*Form.*—Uniform; unsymmetrical; broadly ovoid; sides unequal.

*Suture.*—An inconspicuous line extending from base over entire circumference, but being discontinuous at apex.

*Ventral surface.*—Slightly lipped at one side.

*Cavity.*—Flaring, with suture showing on one side. Depth—about ¼ inch. Breadth—about ½ inch. Markings—slight.

*Base.*—Rounded

*Apex.*—Depressed.

*Stem.*—Stout; glabrous; about ¾ inch long; medium adherence to stone.

*Skin.*—Thin; tender; bitter; free; slight tendency to break during dry seasons. Color—red-purple, corresponding to Dahlia Purple, Plate 931/1, with moderate down which does not roll up when rubbed.

*Flesh.*—Color—red-purple throughout, corresponding to Oxblood Red, Plate 00823. Amygadalin—wanting. Juice—abundant; rich. Texture—melting. Fibres—few; coarse. Ripens—earliest at apex. Flavor—delicate; sweet and aromatic. Aroma—wanting. Eating quality—best.

Stone: Central; semi-free.

*Fibres.*—Long on sides toward base; part from flesh smoothly.

*Size.*—Small.

*Length.*—About ⅞ inch.

*Thickness.*—About ½ inch.

*Form.*—Oval; cunate toward base.

*Base.*—Oblique.

*Hilum.*—Broad.

*Apex.*—Rounded.

*Sides.*—Equal.

*Surface.*—Regularly furrowed near base.

*Ridges.*—Rounded.

*Dorsal edge.*—Full, with shallow groove and continuous ridges on either side.

Use: Market; dessert; culinary; canning.

Keeping quality: Good.

Shipping quality: Good.

Disease resistance: Good resistance to *Xanthomonas pruni* spot, as well as good resistance to other diseases to which plum varieties in general are normally subject, as determined by comparison with other varieties grown at Ohaupo, New Zealand, and by the fact that the fruit of my new variety has always been completely free from diseases without spraying over a prolonged period of years.

I claim:

A new and distinct variety of plum tree, substantially as herein shown and described, characterized particularly as to novelty by the general resemblance of the tree and fruit to the tree and fruit of the variety known in New Zealand as "Purple King" or "Maynard" (both unpatented), but being especially distinguished therefrom by the red flesh color throughout the fruit, said fruit also having a superior flavor and having very good resistance to *Xanthomonas pruni* spot, as well as good resistance to all other diseases to which plum varieties in general are normally subject in New Zealand.

No references cited.

ABRAHAM G. STONE, *Primary Examiner.*